US011992389B2

(12) United States Patent
Burge (10) Patent No.: US 11,992,389 B2
(45) Date of Patent: May 28, 2024

(54) EARWAX REMOVAL DEVICE

(71) Applicant: Burgeoning Technologies, LLC, Lakeland, TN (US)

(72) Inventor: Scott Burge, Lakeland, TN (US)

(73) Assignee: Burgeoning Technologies, LLC, Lakeland, TN (US)

( * ) Notice: Subject to any disclaimer, the term of this patent is extended or adjusted under 35 U.S.C. 154(b) by 128 days.

(21) Appl. No.: 17/681,160

(22) Filed: Feb. 25, 2022

(65) Prior Publication Data
US 2023/0270594 A1 Aug. 31, 2023

(51) Int. Cl.
*A61F 11/00* (2022.01)

(52) U.S. Cl.
CPC .................. *A61F 11/006* (2013.01)

(58) Field of Classification Search
CPC .............. A61F 11/006; A61F 13/38; A61F 2230/0091; A61B 17/221
See application file for complete search history.

(56) References Cited

U.S. PATENT DOCUMENTS

| | | | |
|---|---|---|---|
| 4,497,186 A * | 2/1985 | Mason | A44C 7/00 D11/78 |
| 9,918,878 B2 | 3/2018 | Burres | |
| 10,154,927 B2 | 12/2018 | Fahn et al. | |
| 10,238,545 B2 | 3/2019 | Kraitzer et al. | |
| 10,758,666 B1 * | 9/2020 | Schultz | A61M 3/0287 |
| 10,813,792 B2 | 10/2020 | Khademhosseini | |
| 2009/0240264 A1 * | 9/2009 | Tuval | A61B 17/0469 606/148 |
| 2012/0136350 A1 * | 5/2012 | Goshgarian | A61B 18/1492 606/41 |
| 2012/0265222 A1 * | 10/2012 | Gordin | A61B 17/06166 606/148 |
| 2012/0296355 A1 | 11/2012 | Burres | |
| 2013/0085458 A1 * | 4/2013 | Manke | A61M 5/31511 604/228 |
| 2014/0188138 A1 * | 7/2014 | Melsheimer | A61B 17/0483 606/144 |

(Continued)

FOREIGN PATENT DOCUMENTS

| | | |
|---|---|---|
| EP | 3076910 B1 | 9/2020 |
| FR | 2600883 A1 | 1/1988 |

(Continued)

*Primary Examiner* — Anh T Dang
(74) *Attorney, Agent, or Firm* — Capitol City TechLaw (57) ABSTRACT

An earwax removal device may include a collector body in the shape of a helix. The collector body may have a lumen that accommodate a control line. The control line may have one end fixed to a distal tip of the helix, and a free end extending from an opening in the proximal end of the helix. The collector body may be removably mounted on the shaft of a handle assembly. The handle assembly may include an actuator mounted for pivot action on the shaft. The free end of the control line may be connectable to the actuator. The collector body and the handle assembly may be inserted into an ear speculum. The ear speculum may be screw coupled to the handle assembly to provide for controlled rotation and insertion of the collector body into an ear canal. The actuator may be pulled in a proximal direction to collapse the collector body and capture earwax that has been scraped from the ear canal.

14 Claims, 6 Drawing Sheets

(56) References Cited

U.S. PATENT DOCUMENTS

| | | | |
|---|---|---|---|
| 2014/0276748 A1* | 9/2014 | Ku | A61B 18/18 606/33 |
| 2015/0142029 A1 | 5/2015 | Fahn et al. | |
| 2016/0135995 A1 | 5/2016 | Burres | |
| 2016/0302973 A1 | 10/2016 | Kraitzer et al. | |
| 2019/0091070 A1 | 3/2019 | Kraitzer et al. | |
| 2019/0125588 A1 | 5/2019 | Fahn et al. | |
| 2020/0093644 A1 | 3/2020 | Kraitzer | |

FOREIGN PATENT DOCUMENTS

| | | |
|---|---|---|
| WO | 2013186781 A1 | 12/2013 |
| WO | 2015083161 A1 | 6/2015 |
| WO | 2018172981 A1 | 9/2018 |

* cited by examiner

EARWAX REMOVAL DEVICE

BACKGROUND

1. Field

Embodiments relate in general to earwax removal devices, and more specifically, to an earwax removal device with a collector body in the form of a helix that is collapsible to capture earwax.

2. Discussion of Related Art

Numerous and varied devices have been employed for removing earwax buildup from the external ear canal. For example, swab-type devices include a collector body in the form of a padding mounted at one end of a shaft. The padding may include features that scrape against the wall of the ear canal to collect wax. Other conventional devices may include structures that limit the insertion depth of the collector body into the ear canal, provide for the delivery of wax softeners into the ear canal, and other mechanisms to facilitate use of the device.

Although conventional earwax removal devices are generally thought to provide acceptable performance, they are not without shortcomings. For example, known devices may provide for controlled insertion, rotation, and extraction of the collector body. However, they do not provide sufficient control over the state of the collector body while positioned within the ear canal. As such, conventional devices may only remove the wax that happens to adhere to the collector body during extraction. Any wax that fails to adhere to the collector body may remain in the ear canal, or it may be pushed farther into the ear canal.

SUMMARY

According to a non-limiting embodiment, a collector for an earwax removal device may include a collector body in the shape of a helix having a distal tip and a proximal end. The collector body may have a lumen that extends from a closed end at the distal tip to an opening in the proximal end. A control line may extend through the lumen. The control line may have a distal end fixed to the distal tip, and a free end extended from the opening.

According to another non-limiting embodiment, an earwax removal device kit may include a collector body in the shape of a helix having a distal tip and a proximal end. The collector body may have a lumen that extends from a closed end at the distal tip to an opening in the proximal end. A control line may extend through the lumen. The control line may have a distal end fixed to the distal tip, and a free end extended from the opening. The kit may also include a handle assembly with a shaft and an actuator mounted for reciprocating action on the shaft. The collector body may be removably mountable on the shaft. The free end of the control line may be connectable to the actuator.

The above and other features, including various and novel details of construction and combinations of parts will be more particularly described with reference to the accompanying drawings. It will be understood that the details of the example embodiments are shown by way of illustration only and not as limitations of the invention. The principles and features of this invention may be employed in varied and numerous embodiments without departing from the scope of the invention.

BRIEF DESCRIPTION OF THE DRAWINGS

Non-limiting embodiments will become more fully understood from the detailed description below and the accompanying drawings, wherein like elements are represented by like reference numerals, which are given by way of illustration only and thus are not limiting of the present invention.

FIG. 8 also shows internal features in broken lines.

DESCRIPTION OF NON-LIMITING EMBODIMENTS

Throughout this disclosure, terms relating to spatial directions (e.g., upper, top, lower, bottom, front, forward, rear, rearward, proximal, distal, etc.) are used for convenience in describing features or portions thereof, as shown in the figures. These terms do not, however, require that the disclosed structure be maintained in any particular orientation.

Figure 1:
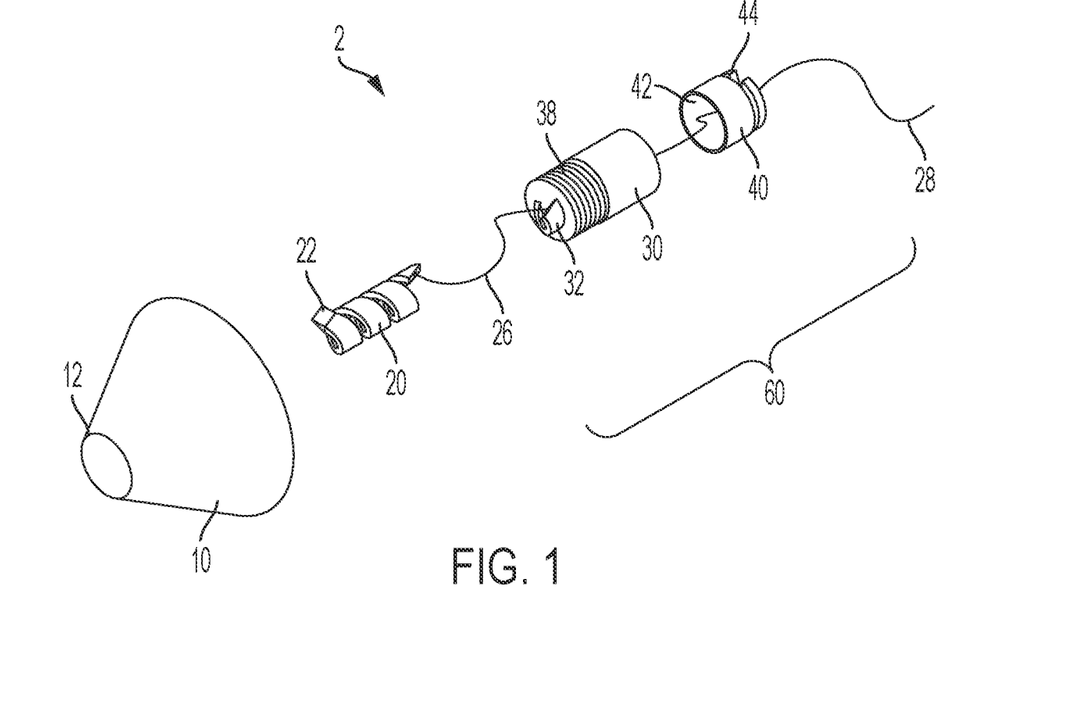
FIGS. 1-3 are exploded views of an earwax removal device according to a non-limiting embodiment, but taken from different viewing angles.
Figure 2:
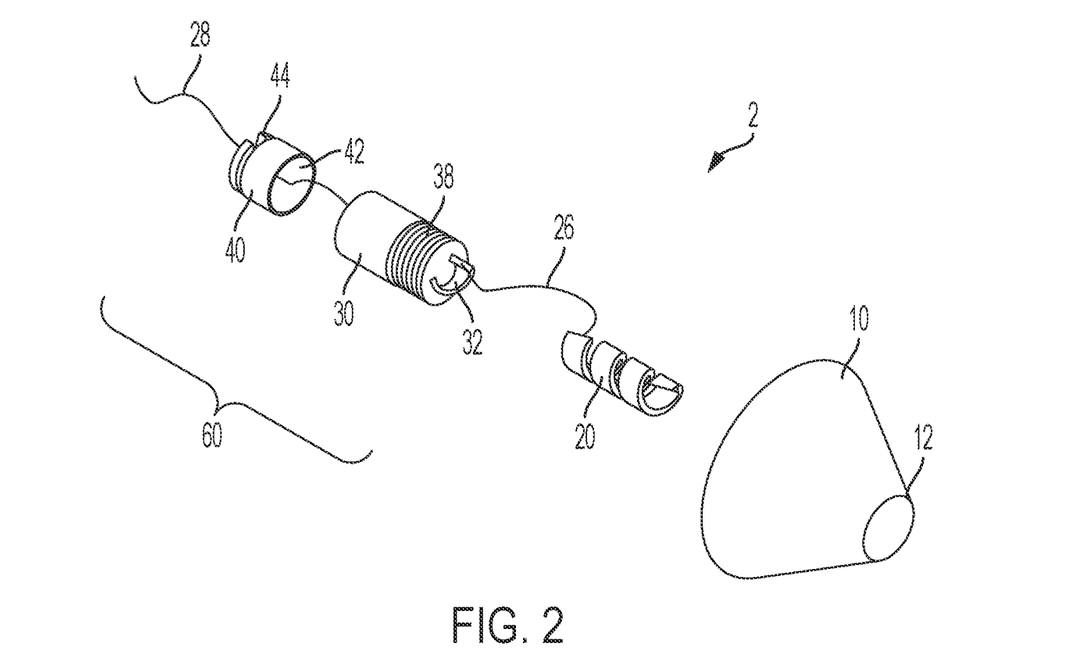
Figure 3:
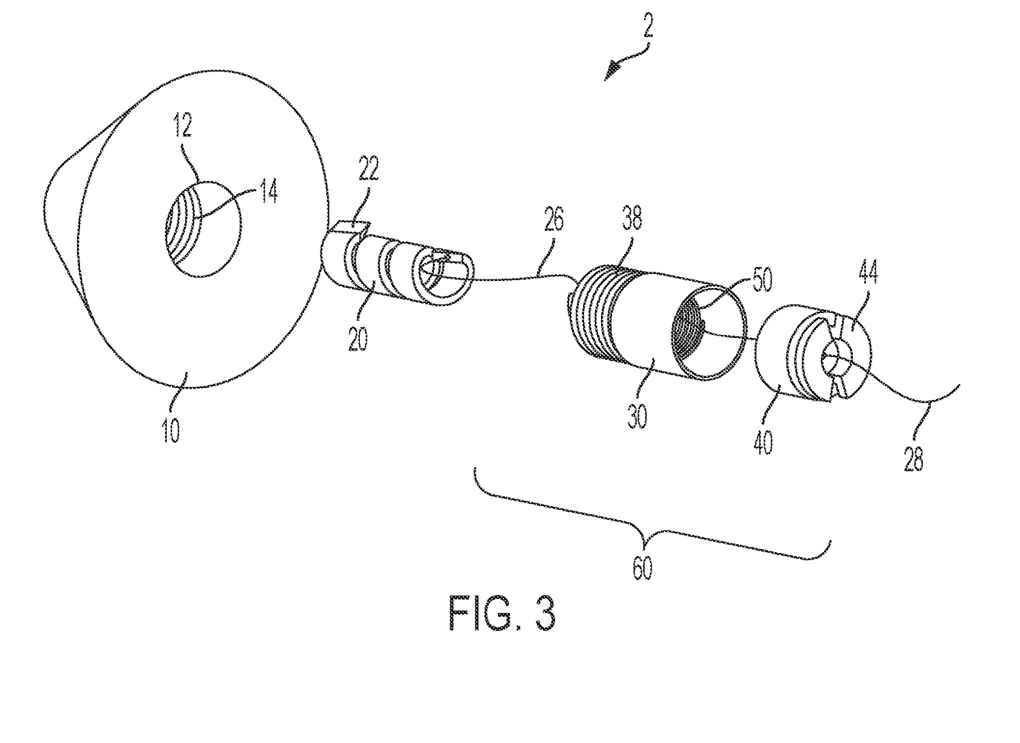

With reference to FIGS. 1-3, the earwax removal device 2 includes an ear speculum 10, an elastic collector body 20, and a handle assembly 60 with an actuator 40 mounted on a shaft 30. FIGS. 1-3 illustrate the earwax removal device 2 in a disassembled condition.

The Collector Body

The collector body 20 is in the shape of a helix with a distal tip 22 that functions to scrape wax from the wall of the ear canal. In the illustrated embodiment, the helix is right-handed, which means that the helix would be rotated in a clockwise fashion for the distal tip 22 to scrape wax. It is readily apparent that in an alternative embodiment, the helix could be left-handed. In the illustrated embodiment, the helix includes three full turns that have a constant curvature and a constant pitch, but the invention is not limited in this regard. The helix may include more or less than three turns and the curvature and the pitch may be varied as desired.

The collector body 20 has a rectangular cross-sectional shape, such that the radial outward facing surface and the radial inward facing surface are parallel to each other, and the shorter side surfaces facing in the longitudinal direction are parallel to each other. It will be appreciated that the helical collector body 20 may have an alternative cross-sectional shape. In use, the radial outward facing surface confronts and abuts against the interior wall of the ear canal.

Figure 4:
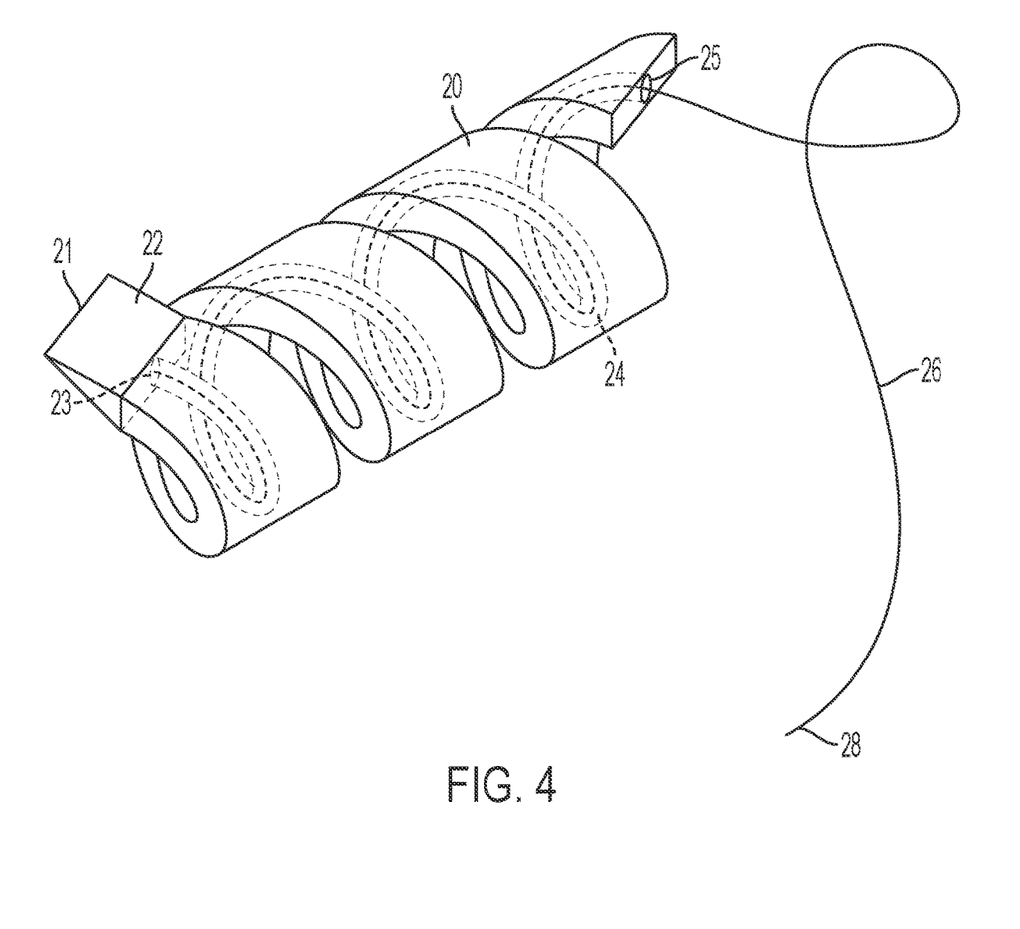
FIG. 4 is a perspective view of an example collector body and showing internal features in broken lines.

With reference to FIG. 4, the distal tip 22 tapers to a leading edge 21. The distal tip 22 projects slightly from the helix curvature in a radial outward direction (out of the plane of the drawing sheet of FIG. 4). This may ensure a desirable contact between the distal tip 22 and the wall of the ear canal, thereby allowing the distal tip 22 to scrape or peel wax from the ear canal wall and allowing the helix to go around the wax.

The collector body 20 includes a lumen 24 that extends from a closed end 23 at the distal tip 22 and spirals through the helix. The lumen 24 has an opening 25 at a proximal end of the helix. The lumen 24 is shown in broken lines for understanding, even though it is hidden from view on the inside of the strip of material forming the helix. The lumen 24 loosely accommodates a control line 26. The control line 26 extends completely through the lumen 24, and has a distal end (not shown) that is fixed to the distal tip 22 of the helix. For example, the distal end of the control line 26 can be glued to or otherwise anchored within the distal tip 22. The control line 26 has a proximal, free end 28 that extends from the opening 25 of the lumen 24.

The collector body 20 may be fabricated from a material that can elastically deform. Such materials can compress and expand to provide a desired fit of the collector body 20 as it moves through and follows the path of the ear canal. By way of example only, such materials may include, but are not limited to, silicone, cellulose, polyurethane, polyethylene, polyamide, polypropylene, and any combination thereof.

The collector body 22 may be fabricated using conventional manufacture techniques. Such techniques may include, but are not limited to, compression molding, extrusion molding, and injection molding. The control line 26 may be provided in the lumen 24 and fixed to the distal tip 22 during or after molding.

The control line 26 extends from the collector body 20 and through the shaft 30 and the actuator 40 of the handle assembly 60. Except for the distal, fixed end, the control line 26 may slide in the lumen 24 and through the shaft 30 and the actuator 40. The free end 28 of the control line 26 extends from the actuator 40 when the helix is mounted on the shaft 30.

The control line 26 may be fabricated from numerous and varied materials, such as metal, plastic, nylon, fluorocarbon, polyethylene, polyvinyl chloride, catgut, and other conventional materials. By way of example only, the control line 26 may be a single strand of material, or multiple stands that are braided, twisted, etc.

The Handle Assembly

The handle assembly 60 includes the shaft 30 and the actuator 40. The actuator 40 is mounted on the shaft 30 for reciprocation relative to the shaft 30.

Figure 5:
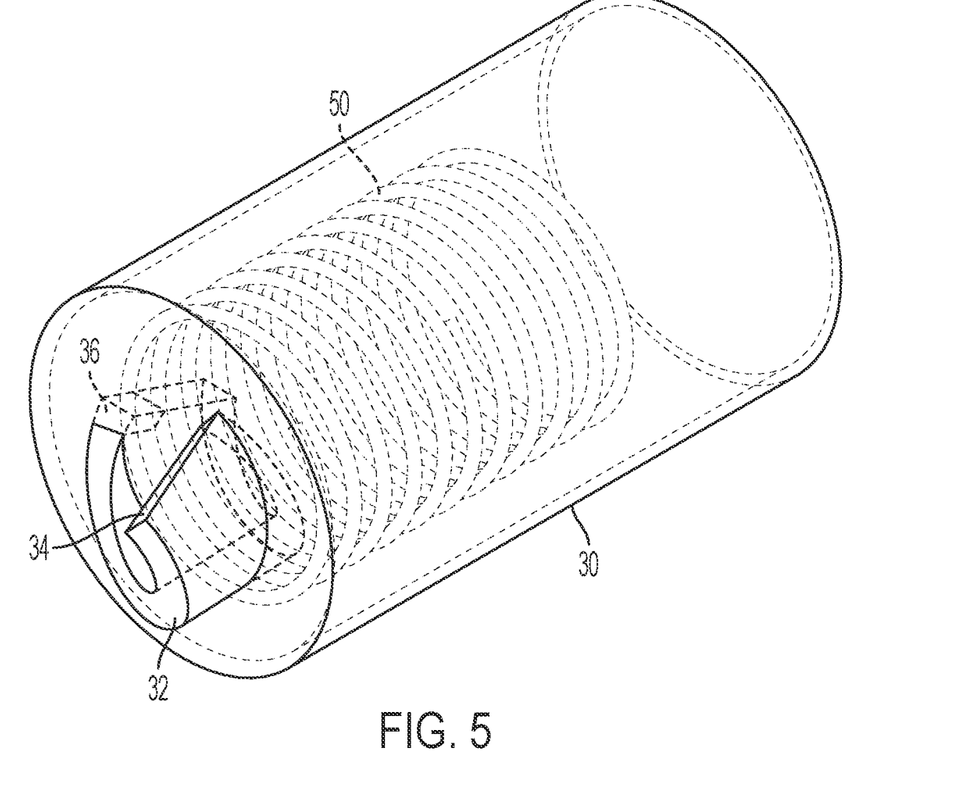
FIG. 5 is a perspective view of an example shaft and showing internal features in broken lines.

With reference to FIG. 5, the shaft 30 may have a hollow cylindrical shape, but the invention is not limited in this regard. The shaft 30 has a distal end with a receiver 32. The receiver 32 has an opening 34 leading to a compartment inside the receiver 32. The opening 34 and the compartment have a shape corresponding to the helix shape of the collector body 20 to allow for removable mounting of the collector body 20 on the shaft 30. Here, the proximal end of the collector body 20 together with the control line 26 can be inserted into the receiver 32, and can be removed therefrom to allow for replacement of the collector body 20 and the control line 26. The insertion depth of the collector body 20 into the receiver 32 can be limited by a stop 36 provided in the compartment. The stop 36 allows the free end 28 of the control line 26 to pass through the receiver 32 and exit from the proximal end of the shaft 30 (to the right in FIG. 5). In the illustrated embodiment, the collector body 20 may be inserted into the receiver 32 through only a fraction of a turn of the helix. The invention is not limited in this regard as the receiver 32 can be shaped and sized to allow for insertion of the collector body 20 through any number of turns (or fractions thereof). As shown in FIGS. 1-3, an external screw thread 38 is provided on the exterior surface of the shaft 30. The external screw thread 38 is not shown in FIG. 5 for clarity.

A coil spring 50 is provided in the hollow interior of the shaft 30. By way of example only, the coil spring 50 may be a tension spring designed to resist stretching. A distal end of the coil spring 50 may be fixed to the distal end of the shaft 30. The coil spring 50 may encircle the portion of the receiver 32 on the interior of the shaft 30, as shown. The proximal end of the coil spring 50 may be fixed to the distal end of the actuator 40.

The actuator 40 is inserted into the open proximal end of the shaft 30 and may reciprocate back-and-forth relative to the shaft 30. The coil spring 50 captured between the shaft 30 and the actuator 40 may influence the reciprocating action of the actuator 40. For example, the actuator 40 can be pulled in the proximal direction relative to the shaft 30 and against the influence of the coil spring 50. When the actuator 40 is released, the coil spring 50 may influence the actuator 40 in the distal direction to its initial condition.

The shaft 30 and the actuator 40 may include features (not shown) that allow and/or guide the reciprocating action but prevent a relative rotation between the shaft 30 and the actuator 40. Such features may include longitudinal splines and corresponding grooves, or other conventional features that are well known in this art. Such conventional features may also be provided to limit the longitudinal travel (or stroke) of the actuator 40 relative to the shaft 30.

The actuator 40 includes a longitudinal through hole that loosely accommodates the control line 26. The distal end of the through hole opens to a conic surface 42. The tapered shape of the conic surface 42 facilitates a replacement procedure in which the control line 26 of a replacement collector body 20 is inserted through handle assembly 60, i.e., through the shaft 30 and the actuator 40 in an assembled together state. The proximal end of the actuator 40 includes a keeper 44. The control line 26 may be wrapped around the keeper 44 and secured by sliding the free end 28 into a notch in the keeper 44.

The component parts of the handle assembly 60 may be fabricated from plastic, rubber, metal, or any other suitable materials that provide the desired structural properties. Materials may also be selected based on their suitability for various methods of sterilization.

The Ear Speculum

The ear speculum 10 is a funnel shaped tube having a distal end (to the left in FIG. 1) that is designed to be inserted into the ear canal. The ear speculum includes a through bore 12 that extends in a longitudinal direction from a narrower distal end to a wider proximal end. The through bore 12 has a cylindrical shape along its entire length, but the invention is not limited in this regard. As best seen in FIG. 3, an internal screw thread 14 is provided on the wall of the through bore 12. The internal screw thread 14 of the ear speculum 10 interacts with the external screw thread 38 of the shaft 30 during use.

The ear speculum 10 may be fabricated from plastic, rubber, metal, or any other suitable materials that provide the desired structural properties. Materials may also be selected based on their suitability for various methods of sterilization.

The Functionality

It will be appreciated that the device may be used by a person without medical training. The device may also be used by a healthcare professional, such as an ENT doctor.

As an initial set up, the collector body 20 is inserted into the receiver 32 of the shaft 30. The control line 26 extends from the collector body 20 and through the handle assembly 60 (the shaft 30 and the actuator 40). The free end 28 of the control line 26 is secured to the keeper 44. In this way, the collector body 20 and the handle assembly 60 may be handled as a unit.

Figure 6:
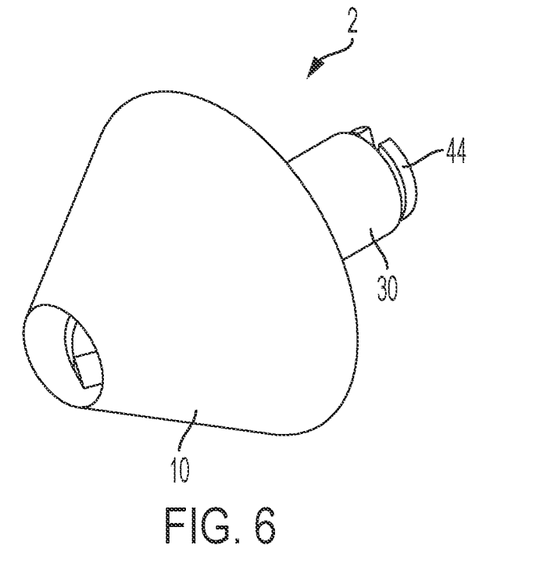
FIGS. 6-8 are perspective views of the earwax removal device in use.

As shown in FIG. 6, the collector body 20 and the handle assembly 60 may be inserted into the ear speculum 10. The control line 26 is hidden from view in FIG. 6.

Figure 7:
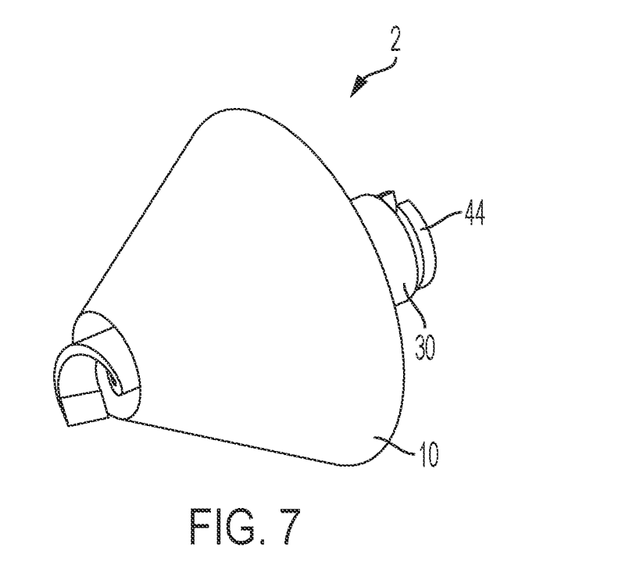

With reference to FIG. 7, the user rotates the handle assembly 60 in a clockwise direction and relative to the ear speculum 10. The collector body 20 rotates together with the handle assembly 60. The relative rotation of the handle assembly 60 causes the external screw thread 38 on the shaft 30 to engage with the internal screw thread 14 on the ear speculum 10. The interaction of the screw threads 14, 38 will cause the collector body 20 to advance in a distal direction as it rotates and begins to protrude from the ear speculum 10. In the condition shown in FIG. 7, the distal end of the ear speculum 10 may be inserted into the opening of the ear canal. The control line 26 is hidden from view in FIG. 7.

The invention is not limited to the sequence of events described above. For example, the ear speculum 10 may be inserted into the ear, followed by inserting the collector body 20 mounted on the handle assembly 60 into the ear speculum 10.

Figure 8:
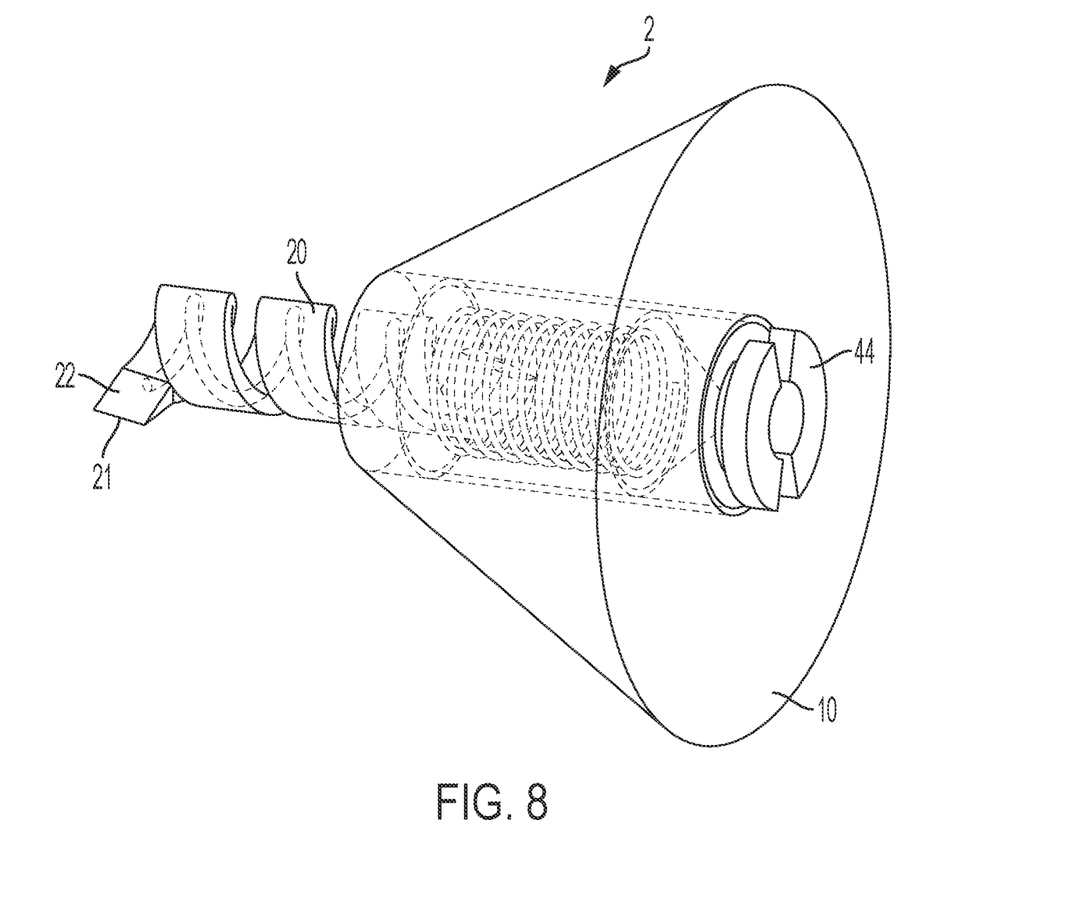

With reference to FIG. 8, further rotation of the handle assembly 60 will cause the collector body 20 to rotate and advance out from the ear speculum 10 and into the ear canal in a controlled fashion. The collector body 20 may bend and flex as it enters into the ear canal to remain substantially parallel to the longitudinal axis of the ear canal at any location along the path of the ear canal. Due to its helical shape and elasticity, the diameter of the collector body 20 may vary and adapt to match and fill the varying diameter of the ear canal. This may maintain the desired surface contacts between the collector body 20 and the wall of the ear canal. As the collector body 20 rotates and advances, the leading edge 21 of the distal tip 22 scrapes and peels wax from the wall of the ear canal. The wax may collect in the interior space of the helix and/or between the turns of the helix. For convenience of illustration, FIG. 8 does not show the control line 26 extending through the interior of the device 2.

The insertion depth of the collector body 20 into the ear canal may be limited by the interaction of the screw threads 14, 38. For example, the screw threads 14, 38 could have thread lengths that would prevent clockwise rotation of the handle assembly 60 relative to the ear speculum 10 once the collector body 20 protrudes a predetermined distance from the ear speculum 10. In this way, the device 2 could be configured to maintain a clearance distance between the collector body 20 and the ear drum.

Once scraping is complete, the user may pull the actuator 40 (together with the control line 26) in the proximal direction relative to the shaft 30 and against the influence of the coil spring 50. The distal end of the control line 26 pulls the tip 22 of the collector body 20 in the proximal direction and relative to the cylinder 30 and thus the ear speculum 10. This causes the collector body 20 to elastically deform and collapse around the wax. The collector body 20 may collapse in the both the longitudinal and radial inward directions. In this way, wax may be captured between the turns of the collector body 20, as well as in the space on the interior of the collector body 20.

While maintaining the actuator 40 in the pulled position, the device 2 is removed from the ear, together with the wax captured in the collapsed collector body 20. When the actuator 40 is released, the coil spring 50 influences the actuator 40 to move distally relative to the shaft 30, thereby allowing the collector body 20 to return to its initial, un-collapsed helical shape.

The components of the earwax removal device 2 may be cleaned and/or sterilized for reuse. In addition, the collector body 20 and the control line 26 can be designed as a single-use, disposable product. The replacement process may involve unscrewing and separating the ear speculum 10 from the handle assembly 60. The control line 26 is unwound from the actuator 40. Next, the collector body 20 may be removed from the receiver 32 of the shaft 30, which would pull the control line 26 from the handle assembly 60.

The replacement collector body 20 would have its own control line 26. The free end 28 of the control line 26 can be pushed through the opening 34 in the receiver 32, and into the interior of the shaft 30. The tapered surface 42 of the actuator 40 may guide the insertion of the free end 28 through the actuator 40. Next, the proximal end of the replacement collector body 20 can be inserted into the receiver 32 of the cylinder 30. The free end 28 of the control line 26 could be drawn to remove slack, and then wound around the keeper 44 of the actuator 40.

Although the foregoing description is directed to non-limiting embodiments of the present teachings, it is noted that other variations and modifications will be apparent to those skilled in the art, and which may be made without departing from the spirit or scope of the present teachings.

The foregoing detailed description of the various embodiments of the present teachings has been provided for the purposes of illustration and description. It is not intended to be exhaustive or to limit the present teachings to the precise embodiments disclosed. Many modifications and variations will be apparent to practitioners skilled in this art. The embodiments were chosen and described to explain the principles of the present teachings and their practical application, thereby enabling others skilled in the art to understand the present teachings for various embodiments and with various modifications as are suited to the particular use contemplated. It is intended that the scope of the present teachings be defined by the following claims and their equivalents.

What is claimed is:

1. A collector for an earwax removal device, the collector comprising:
   a collector body in the shape of a helix having a distal tip and a proximal end;
   wherein the distal tip is provided with means for scraping wax from a wall of an ear canal;
   a helical lumen that extends within the collector body from a closed end at the distal tip to an opening in the proximal end; and
   a control line extending within the helical lumen, the control line having a distal end fixed to the distal tip, and a free end extending from the opening.

2. The collector according to claim 1, wherein the means for scraping is a leading edge of the dista tip.

3. The collector according to claim 2, wherein the distal tip projects from a curvature of the helix in a radial outward direction.

4. The collector according to claim 1, wherein the helix is right-handed.

5. The collector according to claim 1, wherein the helix includes three turns.

6. The collector according to claim 1, wherein the collector body is fabricated from an elastic material.

7. The collector according to claim 6, wherein the collector body is fabricated from silicone.

8. The collector according to claim 1, wherein the free end of the control line is pullable to deform the helix such that the distal tip moves toward the proximal end.

9. An earwax removal device kit comprising:
- a collector body in the shape of a helix having a distal tip and a proximal end, the collector body having a helical lumen that extends within the collector body from a closed end at the distal tip to an opening in the proximal end;
- a control line extending within the helical lumen, the control line having a distal end fixed to the distal tip, and a free end extending from the opening;
- wherein the free end of the control line is pullable to deform the helix such that the distal tip moves toward the proximal end;
- a handle assembly including a shaft and an actuator mounted for reciprocating action on the shaft;
- wherein collector body is removably mountable on the shaft;
- wherein the free end of the control line is connectable to the actuator;
- an ear speculum having a through hole configured to receive the collector body and the handle assembly;
- wherein the through hole of the ear speculum includes an internal screw thread; and
- wherein the shaft includes an external screw thread configured to interact with the internal screw thread of the ear speculum, such that the shaft and the ear speculum are screw coupled together.

10. The earwax removal device kit according to claim 9, comprising a coil spring captured between the shaft and the actuator;
- wherein the actuator is pullable in a proximal direction relative to the shaft and against the influence of the coil spring.

11. The earwax removal device kit according to claim 9, wherein when the collector body is mounted on the shaft and the control line is connected to the actuator, pulling the actuator in a proximal direction will pull the control line such that the distal tip of the collector body moves toward the shaft and deforms the collector body.

12. The earwax removal device kit according to claim 9, wherein the shaft has a hollow cylindrical shape.

13. The earwax removal device kit according to claim 9, wherein the shaft has a distal end with a receiver having a compartment with a shape corresponding to the helix shape of the collector body; and
- wherein the proximal end of the collector body is insertable into the compartment of the receiver.

14. An earwax removal device kit comprising:
- a collector body in the shape of a helix having a distal tip and a proximal end, the collector body having a helical lumen that extends within the collector body from a closed end at the distal tip to an opening in the proximal end;
- wherein the distal tip is provided with means for scraping wax from a wall of an ear canal:
- a control line extending within the helical lumen, the control line having a distal end fixed to the distal tip, and a free end extending from the opening;
- a handle assembly including a shaft and an actuator mounted for reciprocating action on the shaft;
- wherein collector body is removably mountable on the shaft;
- wherein the free end of the control line is connectable to the actuator;
- wherein the actuator is pullable together with the control line to deform the helix such that the distal tip moves toward the proximal end and elastically deforms the collector body in both a longitudinal direction and a radial direction to capture earwax between turns of the helix and in a space on an interior of the helix.

* * * * *